US00PP09667P

United States Patent [19]

Bautista

[11] Patent Number: Plant 9,667

[45] Date of Patent: Oct. 22, 1996

[54] HELICHRYSUM PLANT NAMED HARVEST LEMON

[75] Inventor: Rodolfo V. Bautista, Half Moon Bay, Calif.

[73] Assignee: Bay City Flower Company, Inc., Half Moon Bay, Calif.

[21] Appl. No.: 514,462

[22] Filed: Aug. 17, 1995

[51] Int. Cl.[6] ..... A01H 5/00

[52] U.S. Cl. ..... Plt./68.1

[58] Field of Search ..... Plt./68.1

*Primary Examiner*—James R. Feyrer
*Attorney, Agent, or Firm*—James R. Cypher

[57] ABSTRACT

The present invention relates to a new and distinct variety of the Compositae family, named *Helichrysum bracteatum* cv. 'Harvest Lemon', which originated as a seedling from the inventor's controlled crossing of a generic hybrid designated by the formula *Helichrysum splendidum* (Thunb.) ×*H. bracteatum* (Vent.) with the species *Helichrysum bracteatum* (Vent.).

The new variety is distinguished from *Helichrysum bracteatum* (Vent.) and all other members of the genera known to me by: the color of its flower and buds, in combination with its resistance to the root disease Pythium, its puberlent leaves, its compact growth habit, its ability to grow well in pots, and the ease with which it can be forced to flower outside for sale in the autumn without growth regulators. The new variety further possesses the commercially and aesthetically desirable characteristic of long-lasting flowers and attractive colors.

1 Drawing Sheet

BACKGROUND OF THE INVENTION

The present invention relates to a new and distinct variety of the Compositae family. The new variety was named *Helichrysum bracteatum* cv. 'Harvest Lemon' by the assignee, Bay City Flower Company, Inc. The inventor is Rodolfo Valdoz Bautista of Half Moon Bay, Calif., a citizen of the Philippines.

This new Helichrysum variety originated as a seedling from the crossing by the inventor of a generic hybrid designated by the formula *Helichrysum splendidum* (Thunb.)×*H. bracteatum* (Vent.) and the species *Helichrysum bracteatum* (Vent.) *Helichrysum splendidum (Thunb.)* ×*H. bracteatum* (Vent.) is the seed parent. *Helichrysum bracteatum* (Vent.) is the pollen parent. The controlled hybridization was conducted in Half Moon Bay, County of San Mateo, Calif.

To produce the hybrid identified by the formula *Helichrysum splendidum* (Thunb.)×*H. bracteatum* (Vent.), the inventor first crossed *Helichrysum splendidum* (Thunb.) with *Helichrysum bracteatum* (Vent.). In this cross, *Helichrysum bracteatum* (Vent.) was the pollen parent. From the seedlings of this cross, the inventor selected the individual known to the inventor as '1A93' for its flower color and compact growth habit. The inventor then crossed the individual known to the inventor as '1A93' and identified by the formula *Helichrysum splendidum* (Thunb.)×*H. bracteatum* (Vent.) with *Helichrysum bracteatum* (Vent.). From the progeny of this cross the inventor selected the new variety to be asexually reproduced.

The new variety is particulary suitable for commercial plant culture because of its long-lasting flowers and attractive colors.

The characteristics of the new variety which in combination distinguish it from *Helichrysum bracteatum* (Vent.) and all other varieties known to me are: the color of its flowers and buds, its resistance to the root disease Pythium, its puberlent leaves, its compact growth habit, its ability to grow well in pots in which it can be sold, and the ease with which it can be forced to flower outside for sale in the autumn without growth regulators.

The flower color of the new variety changes as the involucral bracts age. The bud stage is darkest. The tips of the tightly imbricate involucral bracts are red (R.H.S. 47A). As the flower bud begins to open the tips of the involucral bracts lighten to yellow-orange (R.H.S. 19B), while the rest of the involucral bract lightens to yellow (R.H.S. 4B). The lighter yellow color in the center of the bracts is the dominant color of the flower head. The outer involucral bracts on the underside of the mature flower retain the yellow-orange color the bracts possessed when the flower head began opening.

The following table compares the new variety to the closest varieties known to the inventor, according to the new variety's distinguishing characteristics:

| | *H. splendidum* (general characteristics) | *H. bracteatum* (general characteristics) | '1A93' | New Variety |
|---|---|---|---|---|
| mature involucral bracts | various colors | various colors | R.H.S. 4A | R.H.S. 4B |
| involucral bracts at opening | various colors | various colors | R.H.S. 3C | R.H.S. 19B |
| bud color | various colors | various colors | R.H.S. 187B | R.H.S. 47A |
| disease resistance | Pythium | not resistant to Pythium | Pythium | same |
| hirsute leaves | | no | yes | yes |
| suitability for pot culture | average | good | same | same |
| ease of forcing | difficult | generally good | good | same |
| growth habit | spreading | generally compact | compact | same |
| flowering habit | long-lasting | same | 7 weeks | same |

The distinguishing characteristics are retained by asexually reproduced, successive generations. Since the inventor's discovery of the new variety, the assignee, under the direction and control of the inventor at a commercial nursery in Half Moon Bay, Calif., has asexually reproduced the new variety through three successive generations by means of cuttings and has found that the combination of characteristics as herein disclosed remain firmly fixed.

BRIEF DESCRIPTION OF THE DRAWINGS

The accompanying drawings consist of color photographs that show the typical potted-plant form, including the inflorescence, foliage, and flower color development from the bud stage to the mature flower. The colors are represented as truly as possible using conventional photographic procedures.

DETAILED DESCRIPTION OF THE NEW VARIETY

Figure 1:
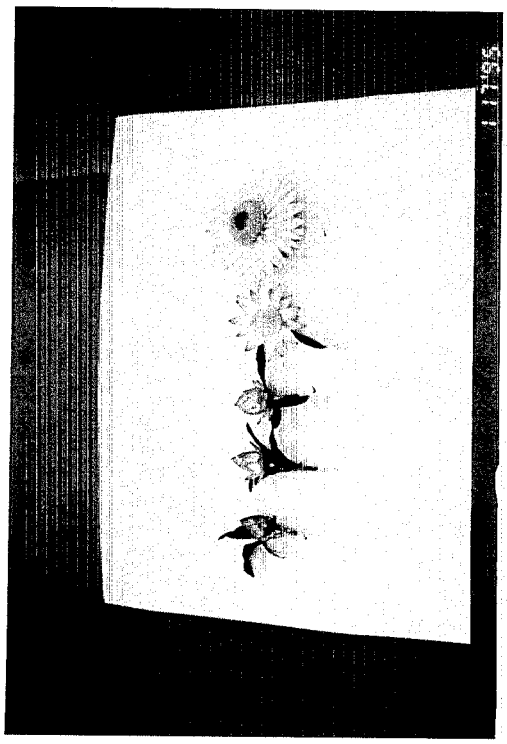
FIG. 1 is a view of individual flowers of the new variety described herein to show the pigmentation pattern of the involucral bracts.
Figure 2:
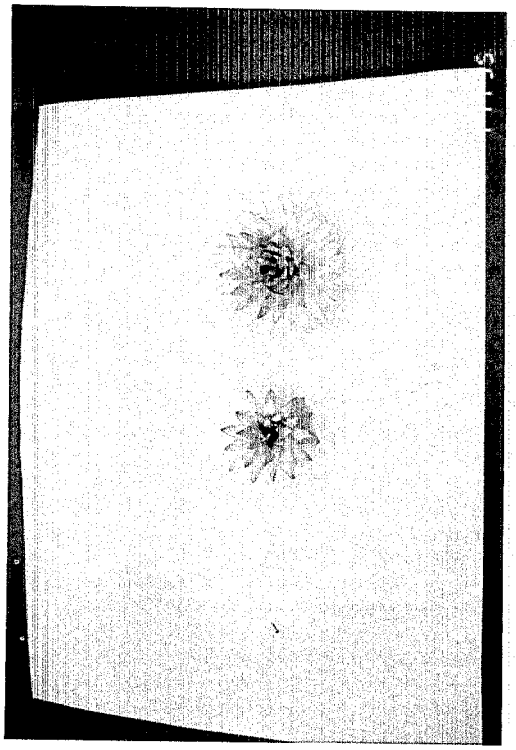
FIG. 2 is a view of the underside of the individual flowers of the new variety described herein to show the pigmentation pattern of the involucral bracts.
Figure 3:
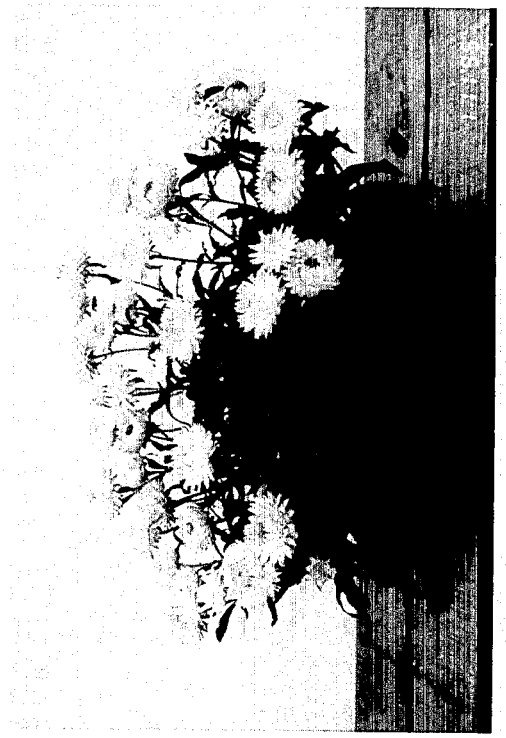
FIG. 3 is a front perspective view of a potted plant of the new variety as described herein, illustrating the overall form and appearance of the plant in full bloom.
Figure 4:
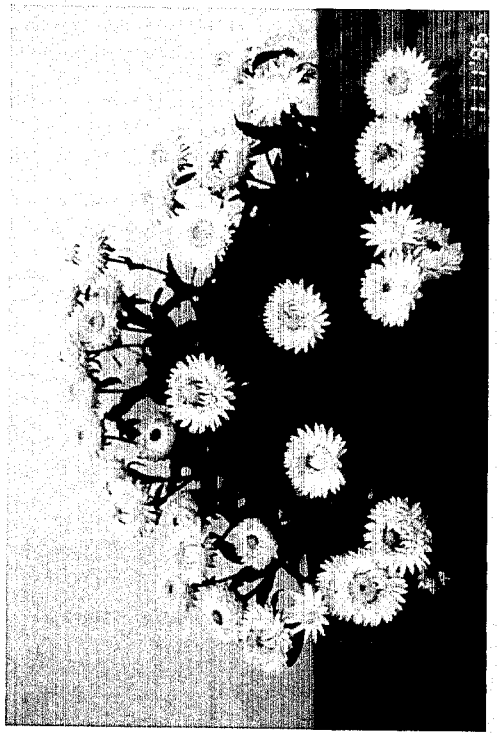
FIG. 4 is a top perspective view of a potted plant of the new variety as described herein, illustrating the overall form and appearance of the plant in full bloom.

The following is a detailed description of the new variety. The plants observed were 24–25 weeks old. The new variety has not been observed under all possible environmental conditions. Color designation and other values stated may deviate slightly from the stated values from flowering to flowering, but the deviations will be within the range expected from varying environmental, seasonal and cultural conditions. The following description is based on observations of optimally fertilized plants grown outside in 15.2 cm pots under the prevailing daylengths and temperatures in Half Moon Bay, Calif., during the summer and autumn months. The average temperature during the day was 60 degrees Farenheit. The average temperature during the night was 51 degrees Farenheit. Color designations were made according to The R.H.S. Colour Chart published by The Royal Horticultural Society of London, England.

THE PLANT

Origin: Seedling.
Parentage:
- *Seed patent.*—*Herichrysum splendidum* (Thunb.)×*H. bracteatum* (Vent.).
- *Pollen parent.*—*Helichrysum bracteatum* (Vent.).

Classification:
- *Botanic.*—*Helichrysum bracteatum* cv. 'Harvest Lemon.'
- *Commercial.*—Strawflower 'Harvest Lemon.'

Form: Upright, compact, biennial shrub.
Height: 33 cm for plants grown in 15.2 cm pots.
Circumference: 132 cm for plants grown in 15.2 cm pots.
Growth: Upright, vigorous growth outdoors with excellent branching; easily forced to bloom without growth regulators.
Stems:
- *Texture.*—Stems are sericeous giving a glaucous appearance; stems very pubescent below the flower with fine cottony hairs that cover the green stem and have a combed smooth appearance.
- *Size.*—Stem width just below flower is 4 mm. Stem width at base of plant is 7 mm.

Foliage:
- *Quantity.*—Abundant.
- *Shape.*—Linear; narrowly acute; margins are repand.
- *Size.*—As large as 17 cm long by 4 cm wide.
- *Texture.*—Viscid; main vein dominates on the underside of leaf and is sunken on the leaf surface.
- *Pubescence.*—Leaf surfaces are puberlent, and sparsely villous; main veins are hirsute.
- *Color.*—Upper leaf surface is R.H.S. 137A (green group); lower leaf surface is R.H.S. 137C (green group).
- *Petiole.*—Nonexistent, semi-amplexicaul.

Disease resistance: Resistant to the root disease Pythium.

THE BUD

Form: Conical, with imbricate involucral bracts.
Size when fully developed:
- *Diameter.*—21 mm.
- *Circumference.*—70 mm.

Texture: Smooth and glossy (waxy).
Rate of opening: Slowly, and in layers, closing at night; fully open in 2–3 weeks.
Involucral bracts:
- *Color.*—Early pigmentation of tips and edges is R.H.S. 47A (red group) which lightens to R.H.S. 19B (yellow-orange group) when bud begins to open.
- *Aspect.*—Thin, dry, membranous.

THE INFLORESCENCE

Form: Flower head is discoid and solitary; usually 1 to 2 buds at the next leaf axis below.
Flower head size:
- *Diameter.*—6 cm.
- *Circumference.*—18.5 cm.

Shape: Circular; involucral bracts are numerous and imbricate.
Appearance: Showy.
Involucral bracts:
- *Color.*—Mature involucral bracts are R.H.S. 4B (yellow group).

Blooming habit: The new variety, when planted in the summer for sale in the Autumn season, can be forced to salable product in 13 weeks under prevailing daylengths and outdoor conditions in Half Moon Bay, Calif.
Persistence: 7 weeks.
Fragrance: None.
Fruit: none.

I claim:

1. A new and distinct hybrid plant variety of the Compositae family substantially as herein shown and described.

* * * * *